(12) United States Patent
Bedding et al.

(10) Patent No.: US 6,407,310 B1
(45) Date of Patent: Jun. 18, 2002

(54) METHOD FOR PREPARING ENTOMOPATHOGENIC NEMATODES FOR STORAGE BY MIXING WITH NON-FIBROUS CELLULOSE PARTICLES OF LESS THAN 300 μM

(75) Inventors: Robin Anthony Bedding, Cook; Simone Daniela Clark, Conder; Michael James Lacey, Hughes; Karen Louise Butler, Ainslie, all of (AU)

(73) Assignee: The Commonwealth of Australia Commonwealth Scientific and Industrial Research Organization, Australian Capital Territory (AU)

( * ) Notice: Subject to any disclaimer, the term of this patent is extended or adjusted under 35 U.S.C. 154(b) by 0 days.

(21) Appl. No.: 09/806,143

(22) PCT Filed: Mar. 28, 2001

(86) PCT No.: PCT/AU99/00829

§ 371 (c)(1),
(2), (4) Date: Mar. 28, 2001

(87) PCT Pub. No.: WO00/18887

PCT Pub. Date: Apr. 6, 2000

(30) Foreign Application Priority Data

Sep. 28, 1998 (AU) .............................................. PP6167

(51) Int. Cl.[7] ...................... A01K 67/00; A01K 67/033; A01N 25/00; C12M 1/00; C12N 1/04
(52) U.S. Cl. ........................... 800/8; 424/405; 435/260; 435/283.1; 435/307.1
(58) Field of Search ........................ 435/243, 289.1, 435/260, 307.1, 283.1; 424/405; 800/8

(56) References Cited

U.S. PATENT DOCUMENTS 4,765,275 A  *  8/1988  Yukawa et al. ................ 119/15
5,042,427 A  *  8/1991  Bedding ....................... 119/6.7
5,183,950 A     2/1993  Popiel et al. .................... 800/2

FOREIGN PATENT DOCUMENTS

| WO | WO85/03412 | * | 8/1985 |
| WO | WO89/07446 | * | 8/1989 |
| WO | WO94/05150 | * | 3/1994 |
| WO | WO94/19940 | * | 9/1994 |

* cited by examiner

*Primary Examiner*—David M. Naff
*Assistant Examiner*—Deborah K Ware
(74) *Attorney, Agent, or Firm*—Sughrue Mion, PLLC

(57) ABSTRACT

Third stage juvenile (J3) entomopathogenic nematodes are prepared for storage by being induced into a state of cryptobiosis. The induction of cryptobiosis is effected by mixing an aqueous cream of the J3 nematodes with anhydrous, small particles (average maximum dimension less than 300 μm) of non-fibrous cellulose. The proportions of the aqueous cream and non-fibrous cellulose particles are such that, after equilibration, the mixture has a water activity in the range 0.80 to 0.995. Preferably an anti-fungal agent is included in the aqueous cream. To store the cryptobiotic J3 nematodes, the mixture is preferably kept in a container, fitted with an attachment which maintains the water activity in the container at a required value. The attachment includes a rigid tube that connects the interior of the container with a chamber that is vented to ambient atmosphere by small apparatus. When in use the chamber contains water-absorbent material saturated with water or with a saturated salt solution, and the tube contains an air-permeable plug. An alternative attachment comprises a plastic envelope, one face of which is stuck to the wall of the container. Small apertures in the face are aligned with apertures in the container wall. Small apertures in the other face connect the inside of the envelope to ambient atmosphere. In use, the envelope contains a water-absorbent material saturated with water or a salt solution, and at least one spacer member.

9 Claims, 2 Drawing Sheets

METHOD FOR PREPARING ENTOMOPATHOGENIC NEMATODES FOR STORAGE BY MIXING WITH NON-FIBROUS CELLULOSE PARTICLES OF LESS THAN 300 μM

TECHNICAL FIELD

The invention concerns the storage of entomopathogenic nematodes for transport or future use. More particularly it concerns the preparation for storage, and also the storage, of the third stage infective juveniles (commonly called "J3" nematodes) of nematodes belonging to the genera Steinernema (synonym Neoaplectana) and Heterorhabditis (synonym Chromonema), at controlled water activities.

BACKGROUND

It is well known that entomopathogenic nematodes in the families Steinernematidae and Heterorhabditidae have considerable potential for the biological control of a number of insect pests. Infective third stage juveniles (J3) of the nematodes (which can survive many weeks in the environment without feeding) are able to seek out an insect, penetrate into the insect's haemocoel and there release specific symbiotic bacteria (Xenorhabdus or Photorhabdus species). The bacteria kill the insect within a day or so and provide suitable conditions for the juvenile nematodes to progress to the adult stage, and for nematode reproduction.

The specification of International Patent Application No. PCT/AU93/00465, which was published as WIPO Publication No. WO 94/05150, contains a comprehensive summary of previously adopted methods for, and details of what was then recent work in, the storage of J3 entomopathogenic nematodes, including a description of an effective technique for the preparation for relatively long term storage of J3 nematodes. That technique involved mixing together an aqueous concentrate of clean J3 entomopathogenic nematodes and substantially anhydrous particles of a highly water-absorbent material, the proportions of the aqueous concentrate and water-absorbent material in the mixture being such that (a) sufficient water is absorbed from the concentrate by the absorbent particles to induce cryptobiosis of the nematodes, and (b) the mixture, after equilibrating, has a water activity in the range of from 0.80 to 0.995. Suitable arrangements for storing the cryptobiotic J3 nematodes at the selected water activity value are also described in WIPO Publication No. WO 94/05150.

DISCLOSURE OF THE PRESENT INVENTION

The first aspect of the present invention is an improvement in what has been, up to now, the preferred technique for preparing J3 entomopathogenic nematodes for storage, as described in WIPO Publication No. WO 94/05150, namely the selection of the water-absorbent material to be used in that method to induce cryptobiosis of the J3 nematodes, and to carry the J3 entomopathogenic nematodes that are in a state of induced cryptobiosis.

In WIPO Publication No. WO 94/05150, it is shown that polyacrylamide gel particles, or particles of starch polyacrylamide gel (optionally with polyacrylamide gel particles also present), or methyl cellulose powder, may be used as the medium both for use in the induction of the state of nematode cryptobiosis and for maintaining a selected water activity during subsequent storage.

In fact, methyl cellulose is not a highly water-absorbent compound and its recitation in WIPO Publication No. WO 94/05150 was inappropriate (being based on anecdotal evidence of methyl cellulose as a water absorbent). Methyl cellulose, which is used as an appetite suppressor, is a chemically derived compound which is soluble in water and which, in the course of dissolving, expands to form a glue-like product. Although anhydrous particles of methyl cellulose can absorb water from an aqueous cream of J3 entomopathogenic nematodes to induce cryptobiosis of the nematodes and establish a mixture that has the desired water activity, (a) the glue-like mass in which the J3 nematodes are distributed prevents air (oxygen) from reaching the nematodes, and (b) if, subsequently, water is added to the mixture of J3 nematodes, water and methyl cellulose, to release the nematodes for spraying, the methyl cellulose, being in solution, cannot be removed by sieving and the glue-like consistency of the mixture clogs the spray. nozzles. In fact, it is now clear that it is impractical to use anhydrous particles of methyl cellulose in the method described and claimed in WIPO Publication No. WO 94/05150.

Anhydrous particles of polyacrylamide gel, and of starch polyacrylamide gel, are significantly better as a storage substrate than attapulgite clay, which has been used previously for this purpose. This is primarily because, when particles of polyacrylamide gel, and of starch polyacrylamide gel, are used as described in WIPO Publication No. WO 94/05150, air is available to the nematodes while in their cryptobiotic state and it is not necessary to cool the nematodes during their storage. When attapulgite clay is used as the storage medium, a layered and compressed mixture of clay and cryptobiotic J3 nematodes is formed. This compressed mixture restricts the availability of air to the nematodes. This mixture, therefore, has to be kept in a refrigerator during storage to reduce the activity (and hence reduce the oxygen intake requirements) of the nematodes. However, the particles of polyacrylamide gel, or of starch polyacrylamide gel, retain a lot of water, particularly when a water activity of about 0.995 is established for the mixture. At this water activity level, particles of polyacrylamide gel, or of starch polyacrylamide gel, retain about 300 times their weight of water, which is really waste material.

There is one (quite old) recorded use of cellulose, in the form of a filter paper, as a medium on which J3 entomopathogenic nematodes can be stored. That disclosure is in the paper by J. F. Howell, entitled "New storage methods and improved trapping techniques for the parasitic nematode Neoaplectana carpocapsae", which was published in the *Journal of Invertebrate Pathology*, Volume 33, pages 155 to 158, 1979. Howell put his J3 nematodes on a filter paper into a cold environment, thus ensuring that they did enter into a protected state, similar to cryptobiosis. However, there was no control of water activity and the J3 nematodes would not have survived if stored at a higher temperature. Moreover, storage of nematodes on a filter paper would not be a commercial proposition. If the nematodes should survive the storage period, they would be difficult to disperse in the field. The fibrous cellulose in a filter paper clogs up a spray nozzle, even when the filter paper is cut into small pieces. Presumably, to disperse the nematodes, they would have to be formed into a sprayable aqueous suspension by (i) immersing the filter papers containing the stored nematodes in water until the nematodes become active and leave the filter paper, then (ii) removing the filter papers from the dilute suspension of nematodes thus obtained, and (iii) optionally concentrating the suspension by decantation after allowing the nematodes to settle, or by collection of the nematodes using a muslin cloth, to form a sprayable suspension of J3 nematodes.

The present inventors have discovered that small particles (that is, particles having a size of less than 300 microns (300 μm), preferably less than 200 microns, more preferably less than about 100 microns, and most preferably less than 50 microns) of non-fibrous cellulose can be used as a storage medium for J3 entomopathogenic nematodes and that a mixture of J3 nematodes and such particulate cellulose, when suspended in water, is sprayable. The small particles of cellulose, unlike anhydrous particles of methyl cellulose, are not soluble. Cellulose particles are not highly water-absorbent (they absorb about 2.2 times their weight of water when establishing a water activity of about 0.995). When small anhydrous particles of cellulose are mixed with an aqueous cream of J3 entomopathogenic nematodes to induce cryptobiosis of the nematodes and establish a desired water activity, a fluffy mixture is produced, in which air (oxygen) is available to the J3 nematodes in the mixture. Thus the mixture (a) does not include a large amount of waste water (which is the case when particles of polyacrylamide gel, or of starch polyacrylamide gel, are used), and (b) does not have to be cooled during storage to reduce the activity of the nematodes (which is necessary when the cryptobiotic nematodes are stored in a layered mixture with attapulgite clay). Furthermore, it has been found that J3 nematodes stored in this manner (preferably with the addition of an antifungal agent) can be distributed in the field simply by adding the stored mixture of nematodes (in a state of cryptobiosis) to clean water, waiting for a period of from 5 minutes to one hour for the nematodes to reach their full activity level, then spraying the suspension of nematodes and particulate cellulose.

Experiments conducted by the present inventors have shown that J3 entomopathogenic nematodes can be stored effectively for extended periods by using the method described in WIPO Publication No. WO 94/05150, with small diameter particulate non-fibrous cellulose material substituted for the highly water-absorbent material of that method.

Hence, according to the first aspect of the present invention, a method of preparing third stage infective juveniles (J3) of entomopathogenic nematodes for storage comprises: mixing together an aqueous concentrate of clean J3 entomopathogenic nematodes and substantially anhydrous small particles of non-fibrous cellulose, the particles having an average maximum dimension which is less than 300 $\mu$m, the proportions of the aqueous concentrate and particulate cellulose in the mixture being such that (a) sufficient water is absorbed from the concentrate by the cellulose particles to induce cryptobiosis of the nematodes, and (b) the mixture, after equilibrating, has a water activity in the range of from 0.80 to 0.995.

As noted above, the preferred maximum dimension of the cellulose particles is less than 200 microns and more preferably less than 100 microns. Most preferably the cellulose particles have a diameter of less than 50 microns. A particularly useful form of non-fibrous cellulose is the BO-2 grade cellulose available from Cellulose-Füllstoff-Fabrik GmbH & Co KG, generally known as "CCF", of M önchengladbach, Germany, under the trade mark TECHNOSEL 40. That BO-2 grade cellulose, it is believed, is produced by milling a cellulose pulp that has been treated to remove lignins and other impurities. It consists of cellulose particles which have a generally rectangular cross-section with an average maximum dimension of about 32 microns (32 $\mu$m).

Preferably the water activity of the equilibrated mixture of J3 nematodes, particulate cellulose and water is in the range of from 0.92 to 0.995, and more preferably the water activity of the equilibrated mixture is from 0.95 to 0.99.

Preferably, an anti-fungal agent is included in the mixture of J3 nematodes, non-fibrous cellulose particles and water.

Embodiments of the first aspect of the present invention will now be described, by way of example only.

DESCRIPTION OF EMBODIMENTS OF THE PRESENT INVENTION

In a series of trials conducted by the present inventors to confirm the efficiency of the present invention, samples of third stage juvenile entomopathogenic nematodes were reared and extracted using the methods described by R A Bedding, M S Stanfield and G W Crompton in the specification of International patent application No. PCT/AU91/00136 (WIPO Publication No. WO 91/15569). However, to perform this invention the nematodes may be reared on insects in vivo or in liquid culture, provided the nematodes (a) are free from appreciable amounts of extraneous matter remaining from the culture medium, and (b) are relatively free from nematode stages other than J3 (preferably no adult nematodes are present and certainly no more than 2 per cent of the nematodes should be adults).

The entomopathogenic nematodes reared for the trials by the present inventors, as in the technique described in the specification of International patent application No. PCT/AU88/00127, were sedimented after washing and the excess water was drained off. The sediment of nematodes was then pumped from settling tanks into sieves lined with cloth through which the water, but not the nematodes, could pass. Water was drained off in this way and further water was removed by stirring the nematode cream while draining. In some trials, still further was removed by gathering up the cloth edges to enclose the nematode mass in the cloth before squeezing out some of the remaining water. The resulting cream of nematodes contained from 0.5 to 3.5 million J3 nematodes per gram, depending upon the species involved and the amount of inter-nematode water remaining. For some experiments, one of various antifungal agents was added to and mixed with the sedimented nematodes while they were still in the tanks. Hence, after removal of much of the surface water (and thus also of most of the antibiotic and/or antifungal agent), some of the antifungal agent remained to be absorbed by the cellulose particles in the induction of cryptobiosis process. The antifungal agents used by the present inventors were copper oxychloride and those marketed under the trade marks Amistar (a brand of azoxystrobin), Benlate, Tecta and Proxel (Some of these fungicides also have bactericidal properties.)

It will be appreciated that methods of rearing the J3 nematodes other than those mentioned above may be used, and that this list of fungicides is not exhaustive but represents the anti-fungal agents used by the present inventors.

The technique usually adopted for combining the nematodes and the absorbent material was as follows. The cellulose particles were weighed and added to the appropriate weight of nematodes. (The appropriate weights were determined by prior experimentation to ascertain which combinations fall within the required range of water activities). The cellulose particles and nematodes were then immediately stirred and mixed together so that the cellulose particles were evenly distributed in the mixture.

The water activity of the mixture of nematodes and cellulose particles has to be in the range of from 0.80 to 0.995. As noted above, the water activity is preferable in the range of from 0.92 to 0.995, and most preferably is in the range of from 0.95 to 0.99.

The required water activity of the mixture is attained quickly, but not immediately. The cellulose particles take up the free surface water of the nematode cream instantaneously, and then absorb water that is released from within the nematodes. Thus, when the free surface water is first taken up, the mixture of J3 nematodes, cellulose particles and water has a water activity lower than its final value, which is attained within one or two hours.

The normal procedure adopted by the present inventors after mixing together a nematode cream and a quantity of anhydrous cellulose particles is to leave the mixture overnight at a temperature in the range of from 15° C. to 23° C. in conditions allowing for aeration but with reduced evaporation. This was. usually achieved by keeping the mixture in a covered container. After this overnight storage period, samples from the mixture of cellulose particles (now swollen with water) and nematodes are placed in a variety of storage containers, each with provision for gaseous exchange between the interior and the exterior of the container (while minimising water loss), so that anaerobic conditions cannot develop within the container.

Now the value of the present invention is in the extended storage of J3 nematodes that it enables. To test this storage period, samples of the equilibrated mixture containing J3 nematodes in a stage of cryptobiosis were placed in various containers. Some of these containers had positive ventilation arrangements (for example, a series of holes in the container). Others were containers which were provided with a membrane, or included a panel, of a material through which air can permeate.

However, new forms of storage container were developed in conjunction with the present invention and those (preferred) new containers constitute the second aspect of the present invention, which is described below.

In some experiments, the containers were stored at the extended storage temperature of the experiment immediately after receiving a sample of the equilibrated mixture of nematodes, water and non-fibrous cellulose particles. In other experiments, the containers were stored firstly at 15° C. for three days and then at the extended storage temperature. In all experiments, the extended storage was effected in a manner such that the water activity of the cellulose/nematodes combination was maintained at a value in the range of from 0.80 to 0.99.

It was noted early in these trials that if the stored J3 ii nematodes were affected by a fungus, the storage period was reduced significantly. To prevent a fungus infection, a fungicide was included in many of the samples tested. Of the fungicides mentioned above, azoxystrobin was preferred, preferably in combination with Proxel (trade mark).

A particularly severe test of the present invention was storage of the cryptobiotic nematodes at 23° C. Normally, it is difficult to store J3 nematodes for more than 2 to 3 weeks at this temperature. Using the present invention, the following storage times were achieved for J3 nematodes:

*Steinernema glaseri*—From 2 to 5 months

*Steinernema feltiae*—From 4 to 5 months

*Steinernema carpocapsae*—About 8 months

*Steinernema scapterisci*—About 9 months

All Heterorhabditis species tested—From 2 to 3 months.

As noted above, cryptobiotic J3 nematodes that have been stored using the method of the present invention can be prepared for distribution in the field simply be adding the stored mixture of nematodes and non-fibrous cellulose to water. The time taken for the nematodes to reach their full activity level depends upon the period for which they have been stored in a cryptobiotic state. Nematodes that have been stored for a long period of time may take up to one hour to regain their full activity level. However, most species of nematodes regain their full activity level within 5 to 10 minutes. The active J3 nematodes, with their storage medium, may then be sprayed in the usual manner, for small particles of non-fibrous cellulose do not clog a spray nozzle.

DISCLOSURE OF THE SECOND ASPECT OF THE INVENTION

The second aspect of the present invention concerns the equipment in which J3 entomopathogenic nematodes in a state of cryptobiosis may be stored.

For long term storage of cryptobiotic entomopathogenic J3 nematodes, the water activity of the storage environment must be maintained at substantially the required value, and there must be oxygen (air) present for the nematodes to respire properly. Allowing adequate aeration results in loss of water from the storage environment. With long term storage, the reduction of water reduces the water activity of the storage environment. This, in turn, results in further desiccation of the J3 nematodes with consequent adverse effects on the nematodes, and their subsequent mortality.

Clearly, it will be advantageous to conserve water in the storage environment while maintaining the appropriate value of water activity, and this is the objective of the second aspect of the present invention.

To achieve this objective, the second aspect of the present invention provides a water activity control attachment for fitting to an aperture of a container to be used for storage of J3 entomopathogenic nematodes in a state of cryptobiosis.

In one form, this attachment comprises a generally rigid tube which:

(a) is adapted to be fitted in an air-tight manner in or over an aperture of the container so that one end of the tube is within the container; and (b) has its other end within a chamber which has at least one small aperture therein which connects the inside of the chamber to the outside air.

When in use to provide water activity control, the tube will contain a plug of an air-permeable material, such as cotton wool, and the chamber will contain a water-absorbent material that has been saturated with water, or with a saturated salt solution if a specific water activity within the storage container is required. For example, if a water activity of 0.97 is to be established, the water-absorbent material may contain a saturated solution of potassium sulphate.

A modified form of this new water activity control attachment has been designed to fit within, and be supported by, the neck of a wide-necked jar which is to be used to store J3 nematodes which are in a state of cryptobiosis. This modified form of water activity control attachment comprises:

(a) an annular chamber adapted to fit within the neck region of a wide-necked jar, the outer diameter of the annular chamber being slightly less than the inner diameter of the neck of the jar; said chamber being open at its top and closed at its base, whereby the central portion of the annular chamber forms a tube coaxial with the neck of said chamber;

(b) a flange extending horizontally outwardly from the top periphery of said chamber, said flange having dimensions such that said flange is adapted to be supported by the upper surface of said neck when said chamber is placed within said neck; and (c) a cap adapted fit over said neck, said cap having at least one small aperture therein.

When this form of attachment is in use, a plug of air-permeable material is inserted into the tube at the centre of the chamber and a water-absorbent material which has been saturated with water or with a concentrated salt solution is placed within the annular chamber.

Another form of water activity control attachment for a container to be used to store J3 entomopathogenic nematodes in a state of cryptobiosis has been devised. This third form of the second aspect of the present invention provides a water activity control attachment for use with a container having at least one aperture in the (or a) wall thereof, said attachment comprising a plastic envelope having a front face and a rear face, a layer of adhesive being applied over at least the region of the rear face which is adjacent to the edge of the rear face; the rear face having at least one aperture therein; and the front face of said envelope having at least one small aperture in the upper region thereof.

When this attachment is used to control the water activity of cryptobiotic J3 entomopathogenic nematodes stored within the container, the envelope is attached, using the adhesive layer, to the wall of the container, that wall having at least one aperture in it, with the aperture (or apertures) in the rear face of the envelope at least partially overlapping the aperture (or apertures) in the container wall. In addition, the envelope will contain a water-absorbent material which has been saturated with water or with a saturated salt solution, and may also contain at least one flexible spacing member to ensure that the front and rear faces of the envelope are separated from each other and the aperture(s) in the front face of the envelope does (do) not overlap the aperture(s) in the rear face of the envelope.

Embodiments of these forms of water activity control attachment will now be described, by way of example only, with reference to the accompanying drawings.

Figure 1:
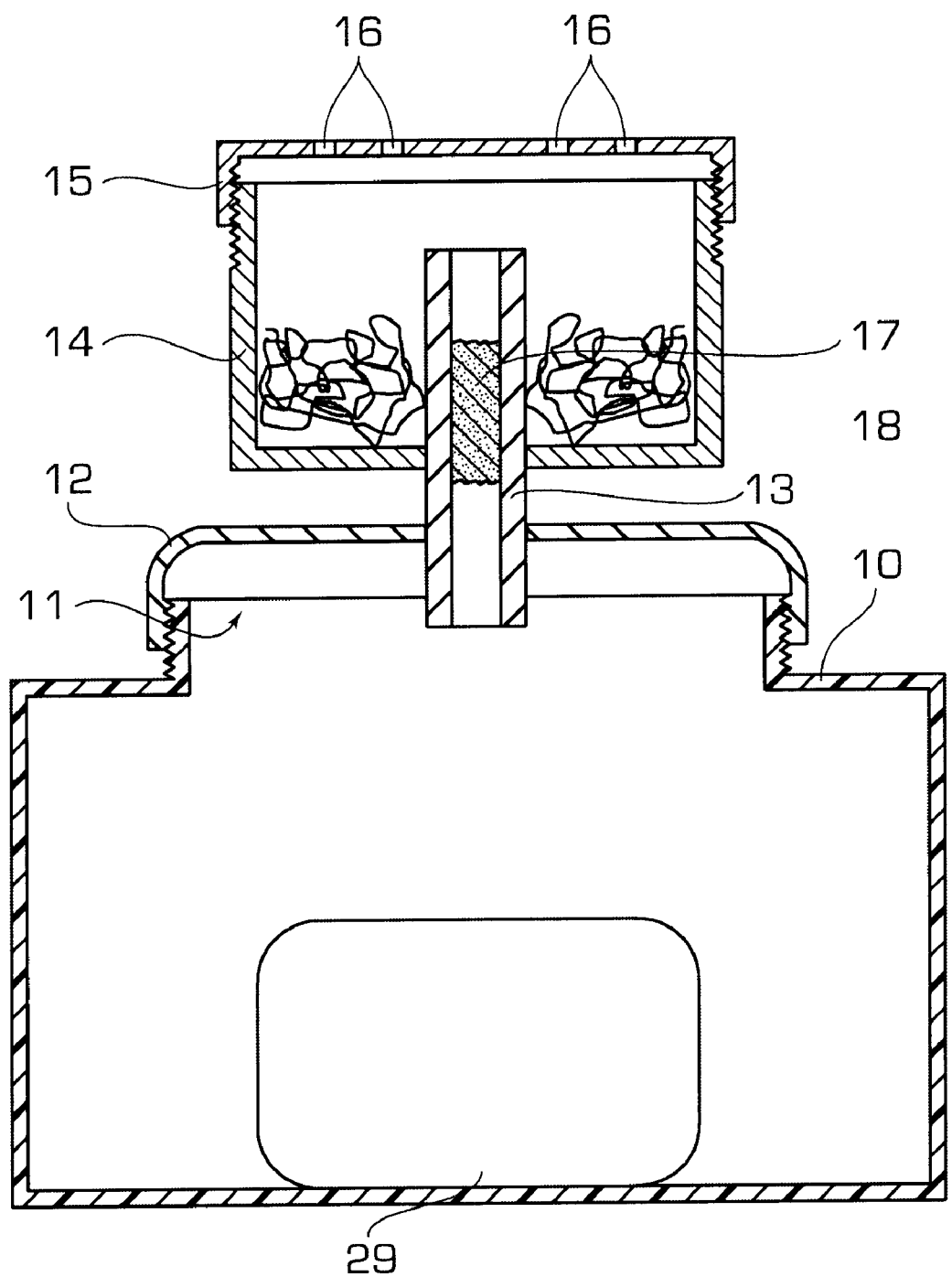
FIG. 1 is partly schematic sectional view of a container being used to store cryptobiotic J3 nematodes, fitted with an embodiment of the first form of water activity control attachment.

In the embodiment illustrated in FIG. 1 of the accompanying drawing, a container 10, having a large aperture 11 in its upper surface, is closed by a screw cap 12. The tube 13 of the water activity control attachment of the present invention is sealed into an aperture which has been cut into the screw cap 12. If the aperture 11 of the container 10 is normally closed by a rubber bung, the tube 13 would be an air-tight fit in an aperture cut into that bung.

The lower end of the tube 13 is within the container 10. The upper end of the tube 13 extends into—and is sealed into—a cylindrical chamber 14, the upper wall of which comprises a screw cap 15. The screw cap 15 contains a number of ventilation apertures 16. If the screw cap 15 is replaced by a suitable lid (which will always be the case if the chamber 14 is not cylindrical), that lid will be provided with the air holes (ventilation apertures) 16.

The chamber 14 contains water-saturated polyacrylamide gel particles 18 (or particles of another suitable water-absorbent material) around the lower region of that part of the tube 13 that is within the chamber 14, to maintain a water activity of 1.00 in the air within the chamber 14. If a saturated salt solution is used to saturate the polyacrylamide gel particles, a different required water activity will be established and maintained within the chamber 14 and—by transfer of air along the tube 13—within the container 10.

Although use of a saturated salt solution enables the establishment of a selected water activity within the chamber 14 and the container 10, the present inventors have discovered that no change in the maximum storage period of any species of entomopathogenic nematode is detectable if the water activity within the container 10 is maintained at 1.00 instead of at the ideal value of, say, 0.96. It is believed that this observation shows that the water activity within a sample 29 of J3 entomopathogenic nematodes stored in a cryptobiotic state with water and a water-absorbent medium (preferably non-fibrous cellulose particles) varies very little unless there is a significant difference between the water activity within the sample and the water activity of the surrounding air.

The tube 13 contains a plug 17 of cotton wool, or other suitable material which permits transfer of air into and out of the container 10, but which prevents microbes and small bugs, dust particles and other particulate contaminant material from entering the container 10.

Variations of the arrangement illustrated in FIG. 1 of the accompanying drawing can be made to suit individual storage containers. For example, if the storage container should have a side aperture instead of a top aperture, the lower part of the tube 13 (that is, that part of the tube 13 that is below the base of the chamber 14) would be longer and would be bent so that the tube could enter the container 10 substantially horizontally, with the chamber 14 performing its normal function as a non-spill water reservoir.

Figure 2:
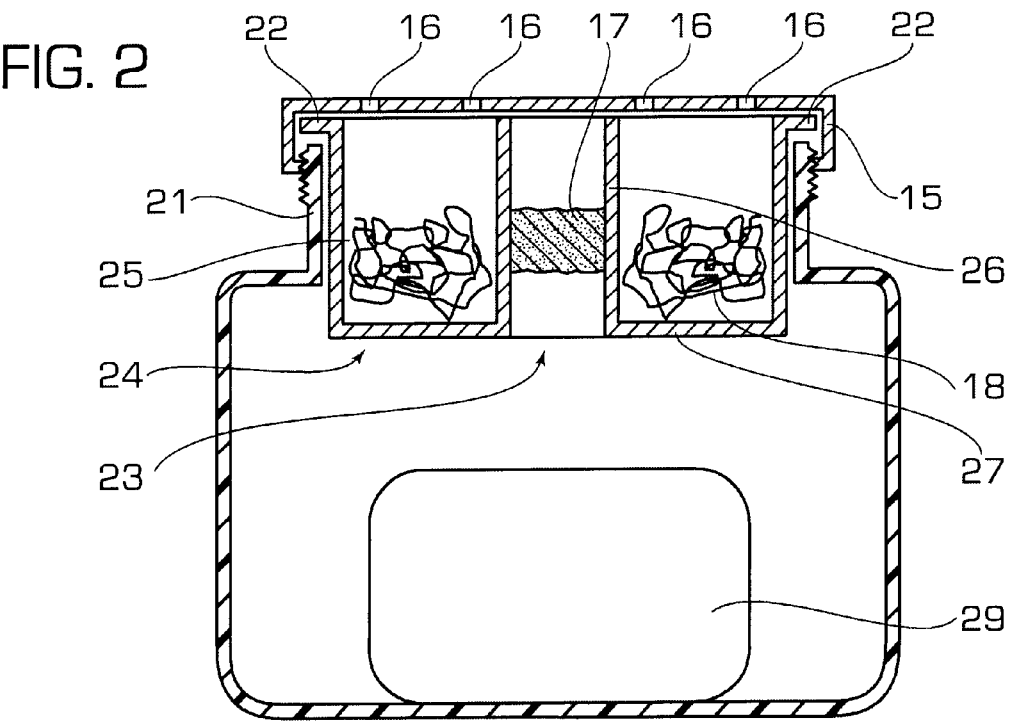
FIG. 2 illustrates, also in the form of a partly schematic sectional view, a container being used to store J3 entomopathogenic nematodes, the container including a modified form of the water activity control attachment illustrated in FIG. 1.

A modified form of the water activity control equipment is illustrated in FIG. 2. In this drawing, a sample 29 of J3 entomopathogenic nematodes is stored within a container 20. The container 20 has a wide neck 21 which is closed by a lid or cap 15. The cap 15 may be screwed onto the neck 21 or it may be a snap-fit over the neck 21. As in the embodiment illustrated in FIG. 1, the cap 15 in FIG. 2 is provided with a number of small ventilation apertures 16. An annular chamber 24 is supported within the neck region of the container 20.

The annular chamber 24 has a substantially vertical outer side wall 25 and a substantially vertical inner side wall 26. The outer diameter of the side wall 25 is slightly less than the inner diameter of the neck 21. The walls 25 and 26 are joined by a circular web portion 27. The chamber 24 is open at its top and the inner side wall 26 forms a tube 23 which contains an air-permeable plug 17. A flange 22 extends outwardly, horizontally, from the top of the side wall 25 for a distance such that (a) the flange 22 overlaps the top surface of the neck 21, and (b) the outer diameter of the flange 22 is less than the inside diameter of the side wall of the cap 15. The annular chamber 24 contains a water-absorbent material 18 (such as polyacrylamide gel particles) saturated with water (or, optionally, with a saturated salt solution) to maintain the water activity of the air above the chamber 24, and thus within the container 20, at a value of 1.00, or the value determined by the use of the salt solution.

The container 24 may be formed from any suitable material by moulding or by pressing.

Figure 3:
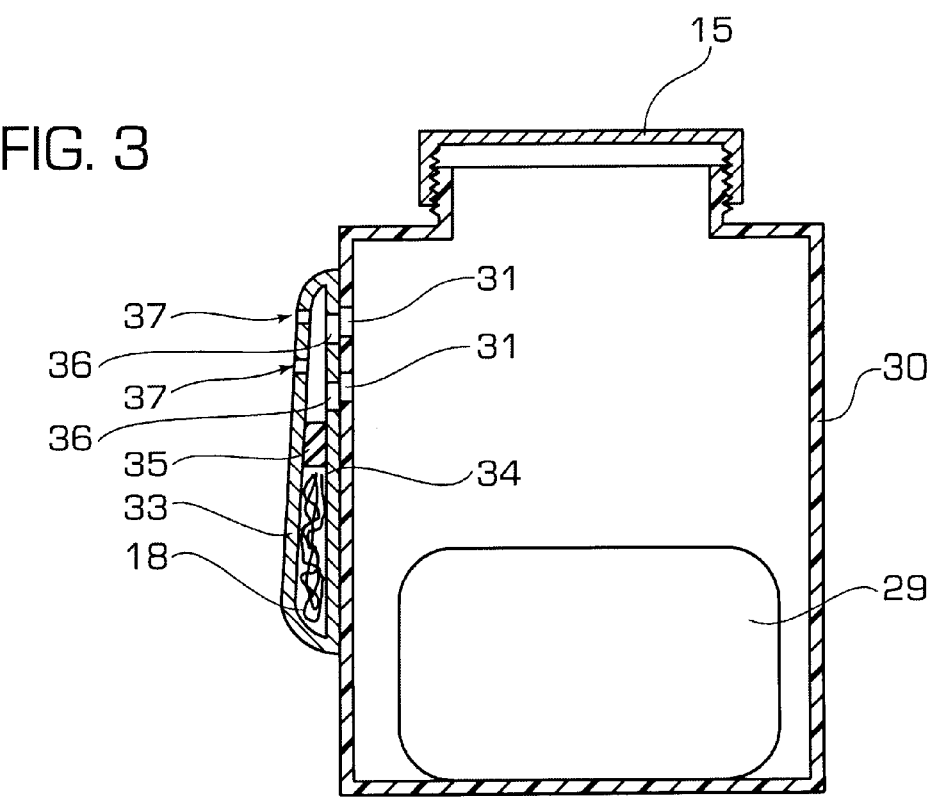
FIG. 3 is a schematic sectional view of a container within which cryptobiotic J3 nematodes and their support medium are to be stored, incorporating an embodiment of the third form of novel water activity control attachment.

The storage arrangement illustrated in FIG. 3 consists of a container 30, with an airtight cap or lid 15. A sample 29 of cryptobiotic J3 nematodes with their support medium, at the required water activity, is within the container 30. The container 30 has a number apertures 31 in its side wall (or in one of its side walls if the horizontal cross-section of the body of the container 30 is rectangular).

A plastic envelope 32, having a front face 33 and a rear face 34, contains (a) polyacrylamide gel particles or starch polyacrylamide gel particles 18, saturated with water or with a saturated salt solution, and (b) a flexible spacer member 35. The spacer member 35, which may conveniently be a strip of the material marketed under the trade mark "SCOTCHBRITE", ensures that the front and rear faces of the envelope do not come into contact with each other during the storage period. The rear face 34 is coated—at least over a region adjacent to the edge of the rear face—with an adhesive material which enables the rear face to be stuck onto the container 30. As shown in FIG. 3, apertures 36 in the rear face 34 of the envelope substantially coincide with (that is, at least partially overlap) the apertures 31 in the container 30. The front face 33 of the envelope has a plurality of small apertures 37 in it, which permit air to enter the envelope and pass through the apertures 36 and 31, and provide a supply of oxygen for the nematodes in the sample 29 while maintaining a water activity of 1.00 (or the value established by the saturated salt solution) within the container 30.

It will be apparent to persons of skill in this field that the above-described methods and various forms of apparatus that constitute the two aspects of the present invention are illustrative only of those aspects of the invention, and that variations to and modifications of the described and illustrated embodiments may be made without departing from the present inventive concepts.

What is claimed is:

1. A method of preparing third stage infective juveniles (J3) of entomopathogenic nematodes of the genera Steinernema (synonym Neoaplectana) and Heterorhabdidtis (synonym Chromonema) for storage, the method comprising: mixing together an aqueous concentrate of clean J3 entomopathogenic nematodes and substantially anhydrous small particles of non-fibrous cellulose, the particles having an average maximum dimension which is less than 300 μm, the proportions of the aqueous concentrate and particulate cellulose in the mixture being such that (a) sufficient water is absorbed from the concentrate by the cellulose particles to induce cryptobiosis of the nematodes, and (b) the mixture, after equilibrating, has a water activity in the range of from 0.80 to 0.995.

2. A method as defined in claim 1, in which the average maximum dimension of the cellulose particles is less than 200 μm.

3. A method as defined in claim 1, in which the average maximum dimension of the cellulose particles is less than 100 μm.

4. A method as defined in claim 1, in which the average maximum dimension of the cellulose particles is less than 50 μm.

5. A method as defined in claim 1, in which said water activity is in the range of from 0.92 to 0.995.

6. A method as defined in claim 1, in which said water activity is in the range of from 0.95 to 0.99.

7. A method as defined in claim 1, in which said aqueous concentrate of J3 nematodes includes an anti-fungal agent.

8. A method as defined in claim 7, in which said anti-fungal agent is azoxystrobin.

9. A method of storing third stage infective juveniles (J3) entomopathogenic nematodes prepared for storage by the method of claim 1, comprising placing the mixture having the water activity in a range of from 0.80 to 0.995 containing the nematodes in a state of cryptobiosis and the non-fibrous cellulose particles in a container and maintaining water activity in the container during storage in the range of from 0.80 to 1.0.

* * * * *

UNITED STATES PATENT AND TRADEMARK OFFICE
CERTIFICATE OF CORRECTION

PATENT NO.     : 6,407,310 B1
DATED          : June 18, 2002
INVENTOR(S)    : Robin Anthony Bedding et al.

It is certified that error appears in the above-identified patent and that said Letters Patent is hereby corrected as shown below:

<u>Title page,</u>
Item [22], PCT Filed, the date should read:
-- September 28, 1999 --

Item [73], Assignee, should read:
-- Commonwealth Scientific and Industrial Research Organisation --

Signed and Sealed this

Eighteenth Day of March, 2003

JAMES E. ROGAN
*Director of the United States Patent and Trademark Office*